United States Patent [19]
Laufer et al.

[11] Patent Number: 5,958,943
[45] Date of Patent: *Sep. 28, 1999

[54] [A]-ANELLATED PYRROLE DERIVATIVES AND THEIR USE IN PHARMACOLOGY

[75] Inventors: Stefan Laufer; Hans Günther Striegel, both of Blaubeuren; Gerd Dannhardt, Mainz, all of Germany

[73] Assignee: Merckle GmbH, Blaubeuren, Germany

[*] Notice: This patent is subject to a terminal disclaimer.

[21] Appl. No.: 08/737,919

[22] PCT Filed: May 31, 1995

[86] PCT No.: PCT/EP95/02077

§ 371 Date: Mar. 28, 1997

§ 102(e) Date: Mar. 28, 1997

[87] PCT Pub. No.: WO95/32970

PCT Pub. Date: Dec. 7, 1995

[30] Foreign Application Priority Data

Jun. 1, 1994 [DE] Germany .............................. 44 19 246

[51] Int. Cl.[6] .......................... A01N 43/42; A01N 43/38; C07F 9/06; C07D 209/02
[52] U.S. Cl. .......................... 514/299; 514/413; 514/414; 514/422; 546/23; 546/24; 546/112; 546/183; 548/455; 548/466; 548/512; 548/516
[58] Field of Search .................................... 546/182, 112, 546/23, 24; 548/455, 466, 512, 516; 514/299, 414, 422, 413

[56] References Cited

U.S. PATENT DOCUMENTS

| | | | |
|---|---|---|---|
| 3,920,672 | 11/1975 | Untch et al. | 260/306 |
| 4,536,512 | 8/1985 | Biftu et al. | 514/413 |
| 4,539,400 | 9/1985 | Fabre et al. | 544/47 |
| 4,546,100 | 10/1985 | Fabre et al. | 514/231 |
| 4,584,297 | 4/1986 | Fabre et al. | 514/226 |
| 4,684,658 | 8/1987 | Fabre et al. | 514/338 |
| 5,552,422 | 9/1996 | Gauthier et al. | 514/368 |
| 5,631,122 | 5/1997 | Mihayashi et al. | 430/506 |

FOREIGN PATENT DOCUMENTS

| | | |
|---|---|---|
| A-0 118 321 | 9/1984 | European Pat. Off. . |
| A-0 147 317 | 7/1985 | European Pat. Off. . |
| A-0 397 175 | 11/1990 | European Pat. Off. . |
| A-24 19 071 | 11/1974 | Germany . |

OTHER PUBLICATIONS

Dannhardt et al., *Archiv der Pharmazie*, 327(8), 1994, 509–514.
Pyl et al., *Justus Liebigs Annalen der Chemie*, 679, 1964, 139–144.
Molloy et al., *Joural of the Chemical Society*, 1995, 65–71.
Galera et al., *Journal of Heterocyclic Chemistry*, 23, 1986, 1889–1892.
Buchan et al., *Journal of Organic Chemistry*, 42(14), 1977, 2448–2454.
Meyers et al., *Chemical Abstracts*, 76(3), 1972, abstract no. 14391j.
Kibirev et al., *Chemical Abstracts*, 61(1), 1964, abstract no. 5629g.
Weuffen et al., *Chemical Abstracts*, 64(1), 1966, abstract no. 5488e.
Alekseeva, *Chemical Abstracts*, 84(17), 1976, abstract no. 120952t.
Druzhinina et al., *Chemical Abstracts*, 80(25), 1974, abstract no. 146165f.
Druzhinina et al., *Chemical Abstracts*, 68(11), 1968, abstract no. 49510j.
Ceder et al., *Chemical Abstracts*, 77(19), 1972, abstract no. 126481r.
Druzhinina et al., *Chemical Abstracts*, 77(13), 1972, abstract no. 88394e.
Alekseeva et al., *Chemical Abstracts*, 77(9), 1972, abstract no. 61153p.
Druzhinina et al., *Chemical Abstracts*, 86(17), 1977, abstract no. 121252t.
Brindley et al., *Chemical Abstracts*, 106(19), 1987, abstract no. 156332c.
Druzhinina et al., *Chemical Abstracts*, 87(1), 1977, abstract no. 5863q.
Artis et al., "Oxidative Radical . . . Three Diastereomers", *J. Org. Chem.*, vol. 59 (1994), pp. 2456–2466.
Pawa et al., "Azomethine Ylide Generation", *Tetra. Lett.*, vol. 48 (1992), No. 36, pp. 7565–7580.
Pizzorno et al., "Novel Synthesis . . . ", *J. Org. Chem.*, vol. 42 (1977), No. 5, pp. 909–910.
Hassner et al., "Intramolecular Formation . . . ", *Tetra. Lett.*, vol. 31 (1990), No. 49, pp. 7213–7214.

*Primary Examiner*—Mukund J. Shah
*Assistant Examiner*—Tamthom N. Truong
*Attorney, Agent, or Firm*—Bacon & Thomas

[57] ABSTRACT

The present invention relates to heterocyclic compounds of the formula

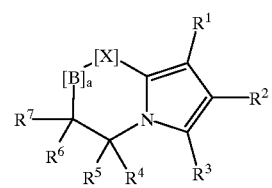

in which $R^1$–$R^7$, B, a and X have the meanings recited in the specification. These compounds are usable in the treatment of diseases of the rheumatoid variety and for the prevention of allergically induced diseases.

12 Claims, 9 Drawing Sheets

[A]-ANELLATED PYRROLE DERIVATIVES AND THEIR USE IN PHARMACOLOGY

This is a 371 application of PCT/EP 95/02077, filed on May 31, 1995.

The invention relates to pyrroles which are anellated at bond a, and their use in pharmacology, as well as to pharmaceutical agents that contain these compounds.

It is known that arachidonic acid is metabolized by different routes. In the cyclooxygenase route, the arachidonic acid is metabolized into prostaglandins under the influence of the enzyme cyclooxygenase. In the lipoxygenase route, the arachidonic acid is metabolized into so-called leukotrienes under the influence of lipoxygenases.

The prostaglandins are involved in the development of inflammation, fever and pain, while the leukotrienes play an important role in the development of asthma, inflammations, and allergies. To fight these symptoms, nonsteroidal anti-inflammatory drugs are used, such as arylethanoic acid derivatives, 2-arylpropionic acid derivatives, and anthranilic acid derivatives. These derivatives inhibit the cyclooxygenase and thus prevent the formation of the prostaglandins from arachidonic acid. Such derivatives are not used without reservations with regard to their side effects, however. Drugs that inhibit lipoxygenase are not available on the market.

European Patent Disclosure EP-A-397 175 describes pyrrolizine compounds of the formula:

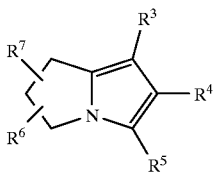

in which two of the radicals $R^3$, $R^4$ and $R^5$ independently of one another stand for H, $C_5$–$C_8$ cycloalkyl, $C_1$–$C_{12}$ alkyl or aryl, which is optionally substituted by one or two radicals, which are selected from the group comprising halogen, $NO_2$, $C_1$–$C_4$ alkoxy, $C_1$–$C_4$ alkyl or phenoxy, and the third of the radicals $R^3$, $R^4$ and $R^5$ stands for CHO, $CO_2H$, $COSC_1$–$C_4$ alkyl or A-X, where A stands for a straight-chain or branched $C_1$–$C_8$ alkylene group or a $C_2$–$C_8$ alkenylene group, and X stands for $CO_2H$, $SO_3H$, CHO, OH, or SH. These compounds are cyclooxygenase- and/or lipoxygenase-inhibitors, and are therefore usable in the treatment of diseases of the rheumatoid variety and for the prevention of allergically induced diseases.

Surprisingly, it has now been found that certain heterocyclic compounds are superior to the above-described pyrrolizine compounds in their effect, and in particular in terms of the analgesic active component, and moreover have a cholesterol-reducing effect.

The subject of the invention is therefore heterocyclic compounds of formula I:

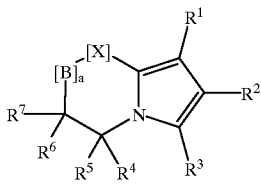

in which
one of the radicals $R^1$, $R^2$ and $R^3$ stands for a mono- or bicyclic aromatic heterocyclic radical which has at least one oxygen, nitrogen and/or sulfur atom and which is optionally condensed with a phenyl or napthyl radical and is optionally substituted by halogen, $CF_3$, alkyl or alkoxy, the second of the radicals $R^1$, $R^2$ and $R^3$ stands for a hydrogen atom, an aryl radical, which optionally has one or two substituents which are selected from the group comprising halogen, pseudohalogen, $CF_3$, $NO_2$, OH, alkoxy, $OCF_3$, alkyl and aryloxy, or for a mono- or bicyclic aromatic heterocyclic radical which has at least one oxygen, nitrogen and/or sulfur atom and which is optionally condensed with a phenyl or napthyl radical and is optionally substituted by halogen, $CF_3$, alkyl or alkoxy, and the third of the radicals $R^1$, $R^2$ and $R^3$ stands for H, CHO, $CO_2H$, COO alkyl, COS alkyl, $COCO_2H$, $COCO_2$ alkyl or A-Y, A stands for $C_1$–$C_8$ alkylene or $C_2$–$C_8$ alkenylene,
Y stands for $CO_2H$, $SO_3H$, $OPO(OH)_2$, $OP(OH)_2$, a group that represents an acid equivalent, COO alkyl, $SO_2O$ alkyl, CHO, OH, or $CONR^8R^9$,
$R^8$ and $R^9$, which may be identical or different, stand for H, alkyl, OH, acyl, $SO_2$ alkyl, or $SO_2$ phenyl, and the alkyl radical of the sulfonyl group is optionally substituted by one or more halogen atoms and the aryl radical is optionally substituted by one or more halogen, $C_1$–$C_8$ alkyl, or $C_1$–$C_8$ alkoxy radicals,
$R^4$, $R^5$, $R^6$ and $R^7$, which may be identical or different, stand for H or alkyl, or two of the vicinal radicals stand for a chemical bond between the two ring atoms to which they are bonded and the other two have the meanings stated, or two of the geminal radicals together with the carbon atom to which they are bonded stand for a carbonyl group,
X stands for $CH_2$, CO, O, S, SO, $SO_2$, or $NR^{10}$, where $R^{10}$ stands for H, alkyl or aryl, which is optionally substituted by halogen, $C_1$–$C_8$ alkyl, or $C_1$–$C_8$ alkoxy,
B stands for $CR^{11}R^{12}$, where $R^{11}$ and $R^{12}$, which may be identical or different, stand for H, alkyl, or together with the carbon to which they are bonded stand for a carbonyl group or its thio analog,
a stands for 0, 1 or 2, and
their optical isomers, salts and esters.

The pharmaceutically compatible salts in the present case can be acid addition salts or base addition salts. Inorganic acids such as hydrochloric acid, sulfuric acid, or phosphoric acid, or organic acids such as tartaric acid, lactic acid, citric acid, malic acid, mandelic acid, ascorbic acid, maleic acid, fumaric acid, gluconic acid, and the like are used for acid addition salts.

Base addition salts include salts of the formula I compounds with inorganic bases such as sodium hydroxide or potassium hydroxide or with organic bases such as monoethanolamine, diethanolamine, or triethanolamine.

The esters of the formula I compounds, in particular include esters that are physiologically easy to hydrolyze, for example alkyl ester, pivaloyloxymethyl ester, acetoxymethyl ester, phthalidyl ester, indanyl ester, and methoxymethyl ester.

The term "alkyl, alkoxy, etc." includes straight-chain or branched alkyl groups such as methyl, ethyl, n-propyl and i-propyl, n-butyl, i-butyl, or t-butyl, n-pentyl, neopentyl, n-hexyl, etc.

Unless otherwise indicated, "alkyl" preferably stands for $C_1$–$C_8$ alkyl, in particular for $C_1$–$C_6$ alkyl, and in particular preferably, for $C_1$–$C_4$ alkyl.

"Aryl" preferably stands for naphthyl and in particular for phenyl.

The term "halogen atom" includes a fluorine, chlorine, bromine, or iodine atom and in particular for a fluorine or chlorine atom. "Pseudohalogen" particularly stands for CN, OCN, SCN, or $N_3$.

"Alkylene" or "alkenylene" stands for straight-chain or branched alkylene or alkenylene groups with preferably 1 to 6 or 2 to 6 and in particular 1 to 4 or 2 to 4 carbon atoms. The alkylene group and in particular the methylene group is preferable.

In particular, a group which represents an acid equivalent is the tetrazolyl group.

"Acyl" stands for RCO, where R preferably has the meanings stated for "alkyl" and "aryl". Acetyl is particularly preferable.

The "aromatic, heterocyclic radical" refers in particular to a 5 and 6-member heterocyclic radical that can be substituted and anellated as indicated above. Examples are a thiophene, pyrrole, imidazole, thiazole, thiadiazole, furan, oxazole, isoxazole, pyridine, pyrimidine, benzofuran, or quinoline radical. If the heterocycle is substituted, 1, 2, or 3 substituents are available, which are selected from the group comprising halogen, $C_1$–$C_8$ alkyl, and $C_1$–$C_8$ alkoxy. A thiophene- or halogen-substituted, in particular chlorine-substituted, thiophene radical, or a furan, pyridine, benzofuran, or quinoline radical, are preferable.

If one of the radicals $R^1$, $R^2$ and $R^3$ means a heterocyclic radical or a substituted aryl radical, then $R^2$ preferably stands for such a radical.

The substituents of the aryl group are preferably selected from the group comprising halogen, in particular fluorine or chlorine, $CF_3$, $NO_2$, and phenoxy. If the aryl group is a phenyl ring, the substituents are preferably situated in the m-position and/or the p-position.

If Y stands for $CONR^8R^9$, then $R^8$ preferably stands for a hydrogen atom and $R^9$ stands for optionally halogen-substituted $SO_2C_1$–$C_8$ alkyl or optionally $C_1$–$C_8$ alkyl-substituted $SO_2$ phenyl, in particular $SO_2CH_3$, $SO_2CF_3$, $SO_2$ phenyl or $SO_2$ tolyl.

A preferred embodiment is the formula I compounds, in which one of the radicals $R^1$, $R^2$ and $R^3$ stands for the aforementioned heterocyclic radical and the second stands for phenyl, for phenyl substituted with one to three halogen atoms or $CF_3$, for thienyl, or for halogen-substituted thienyl.

Preferably the third of the radicals $R^1$, $R^2$, and $R^3$ is situated in the 5-position of the pyrrolizidine structure. In particular, $R^3$ stands for A-Y.

Another set of preferable embodiments is the compounds of the above-mentioned formula I, in which $R^1$ stands for a 5- or 6-member heterocyclic ring, and $R^3$ stands for A-Y, where A and Y have the meanings stated above.

Preferably, A stands for $C_1$–$C_8$ alkylene and Y stands for $CO_2H$, $CO_2C_1$–$C_8$ alkyl, $SO_3H$, $SO_3C_1$–$C_8$ alkyl, $CONR^8R^9$, $COCO_2H$ or $COCO_2C_1$–$C_8$ alkyl, and $R^8$ and $R^9$ independently of one another stand for H, $C_1$–$C_8$ alkyl, $SO_2$ alkyl or $SO_2$ phenyl, and the alkyl radical of the sulfonyl group is optionally substituted by one or more halogen atoms and the aryl radical is optionally substituted by one or more halogen, $C_1$–$C_8$ alkyl, or $C_1$–$C_8$ alkoxy radicals.

In a particularly preferable manner, A-Y stands for $CH_2COOH$ or $CH_2CONHSO_2R$, where R stands for $CH_3$, $CF_3$, phenyl, or tolyl.

X preferably stands for $CH_2$ or S.
B preferably stands for $CH_2$; a preferably stands for 0.

One embodiment is the compounds of the above-mentioned formula I, in which two of the radicals $R^4$ and $R^6$ or $R^5$ and $R^7$ together stand for a chemical bond or in which the radicals $R^4$–$R^6$ stand for H or alkyl. These compounds have the formula:

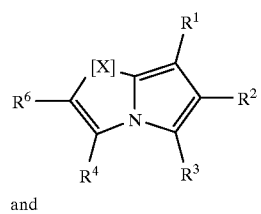

I' and

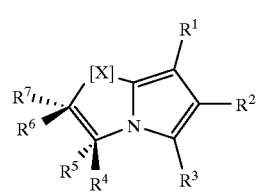

I"

The radicals $R^1$ to $R^7$ and X have the meanings stated above.

In a further preferred embodiment, in formula I", $R^6$ and $R^7$ stand for alkyl and $R^4$ and $R^5$ stand for hydrogen, if X stands for $CH_2$; and $R^6$ and $R^7$ stand for H and $R^4$ and/or $R^5$ stand for alkyl, if X stands for S.

If the compounds according to the invention have asymmetry centers, racemates as well as optical isomers (enantiomers, diastereomers) are included.

The synthesis of the compounds according to the invention takes place analogous to the processes described in FIGS. 1a–c, 2, 3a, 3b, 4, 5a and 5b. These processes are partially described in European Patent Disclosure EP-A-397 175; reference is hereby made to this publication and the literature references mentioned therein.

Initial compounds for the production of the compounds according to the invention are the compounds of formula II:

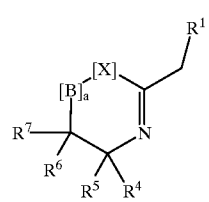

II where $R^1$, $R^4$–$R^7$, and X have the meanings stated above. These compounds are known in the literature or they can be produced analogously to known processes, for example through those described in EP-A 397 175 (X=$CH_2$, CO) or through the reaction of aminothiols, diamines, and amino alcohols derived from D- and L-amino acids with the imide esters of correspondingly substituted carboxylic acids (FIG. 1b: A1/A2).

The formula II compounds are reacted with the corresponding compounds of formula III:

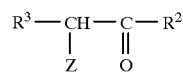

in which Z stands for Cl or Br and $R^2$ and $R^3$ have the desired meanings; see process A. The formula III compounds are likewise known from the literature, some of them being available commercially, or they can be produced analogously to known processes from commercially available precursors; for example, corresponding acetophenones, arylacetaldehydes or deoxybezoines are treated with bromine, or corresponding aryl compounds and aromatic heterocyclic compounds are treated with chloroacetyl chloride (AlCl$_3$) (see: J. J. Riehl, in C. R. Hebd. Seance Acad. Sci Ser. C (1957), 245:1321–1322). The reaction takes place in an inert solvent (such as ethanol, methylene chloride, diethyl ether, tetrahydrofuran) in the presence of a suitable base (such as NaHCO$_3$, triethylamine). If X stands for O, S or NR$^{10}$, the reaction takes place preferably in an ether or aromatic hydrocarbon, such as diethyl ether, benzene or toluene; as a rule, the quaternized intermediate product precipitates out. This product is isolated and dissolved in a chlorinated solvent, such as CH$_2$Cl$_2$, and treated with a base, such as triethylamine.

This reaction produces the formula Ia compounds:

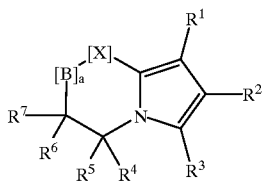

Ia

If at least one of the radicals R$^1$, R$^2$, and R$^3$ stands for a hydrogen atom, compounds of the following formulas IVa–IVc are obtained:

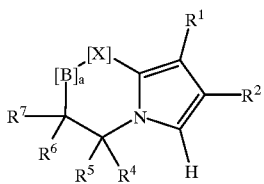

IVa

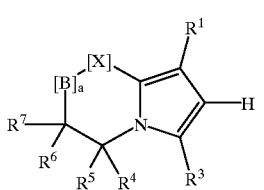

IVb

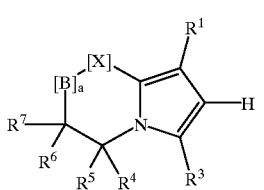

IVc

The compounds of series a, b, or c are derived from this depending on the position of the hydrogen atom.

BRIEF DESCRIPTION OF DRAWINGS

This reaction as well as the reactions mentioned below are outlined in FIGS. 1a–c, 2, 3a, 3b, 4, 5a, and 5b in the example of the compounds of series a. The same is true for the synthesis and derivative production of the compounds of series b and c.

In addition to the process described in European Patent Disclosure EP-A-397 175 (process A), another process (process B) for the composition of heterocycles IVa, IVb, and IVc where X=0, S or NR$^{10}$ is used (FIG. 2): The starting point of this process is correspondingly substituted 2-(5H) furanones (VI), which are produced from carboxylic acid salts of structure V and the halogen aldehydes and halogen ketones of structure III (FIG. 2), analogous to the methods described in the literature (a: Rio, G. and Sekiz, B. Bull. Soc. Chim. Fr. 1976, 1491, 1495. b: Padwa, A., Brookhart, T., Dehm, D., and Wubbels, G., J. Am. Chem. Soc. 1978, 100, 8247, 8259). Analogous to methods known from the literature, these are transformed into 1,5-dihydro-2-pyrrolones (VII or VIII) (c: Matsuda et al. Yakugaku Zasshi 95, [1975] 190, 194 (C. A. 83 [1975] 42 780; d: Rio, G. and Sekiz, B., see above).

Figure 1A:
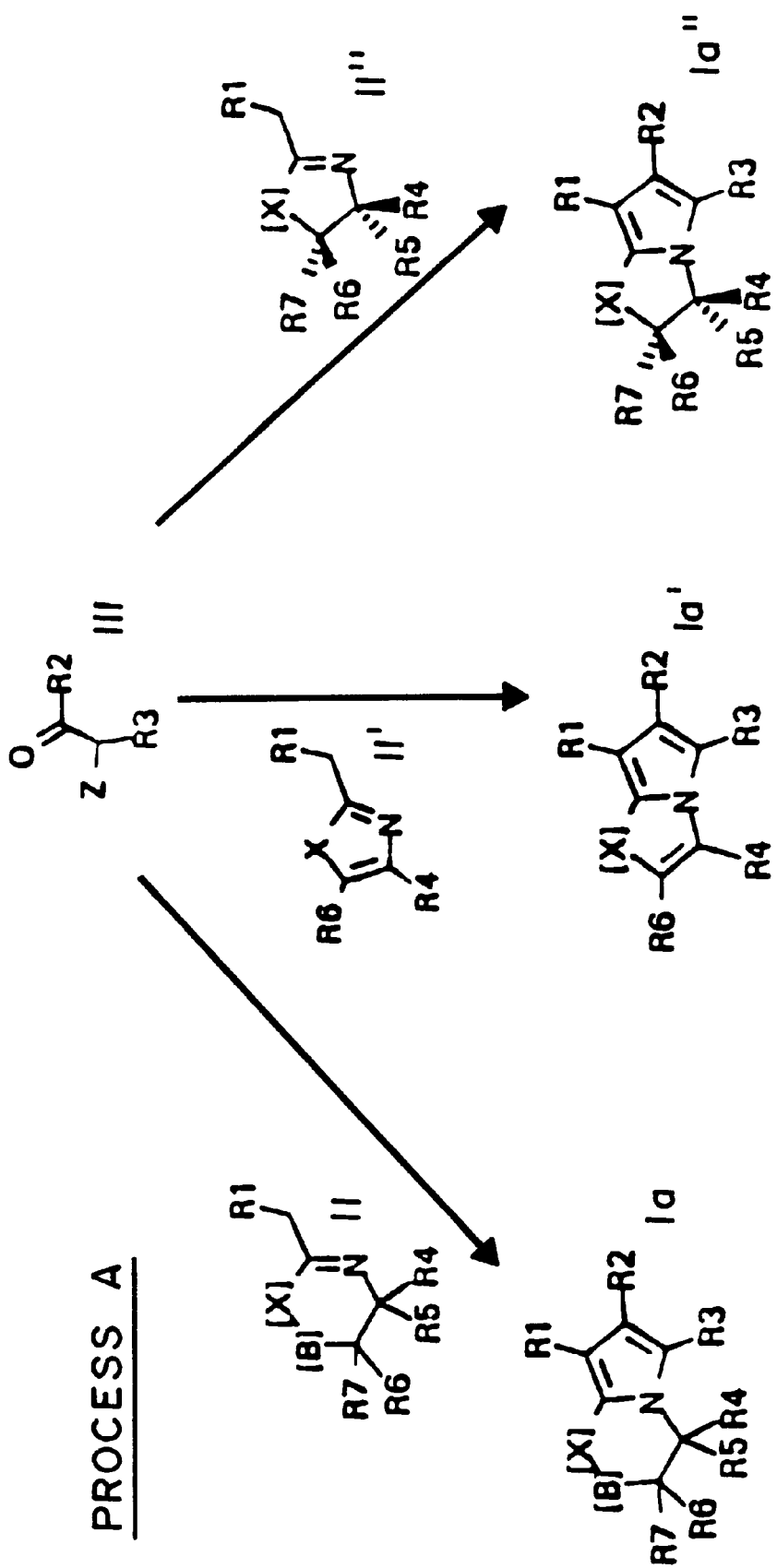
Figure 1B:
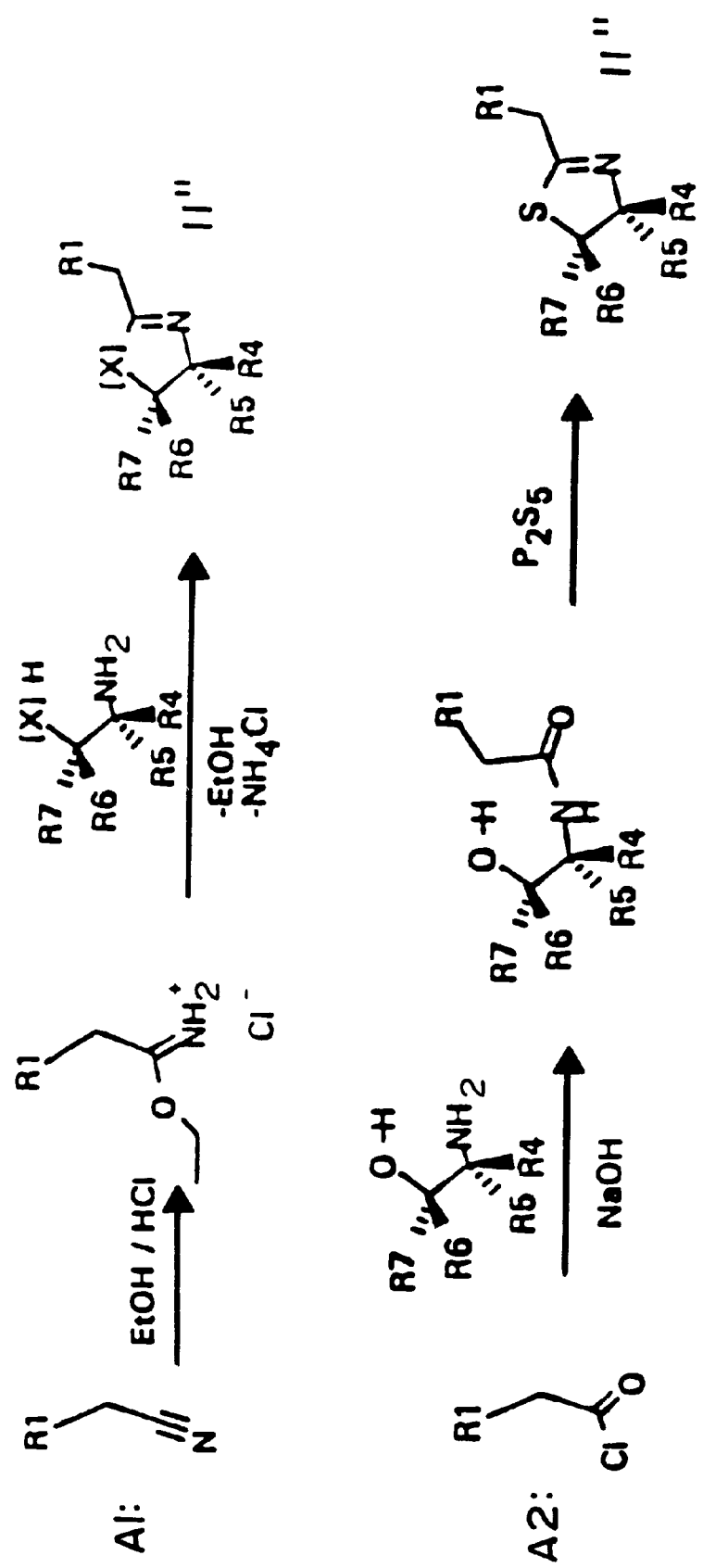
Figure 1C:
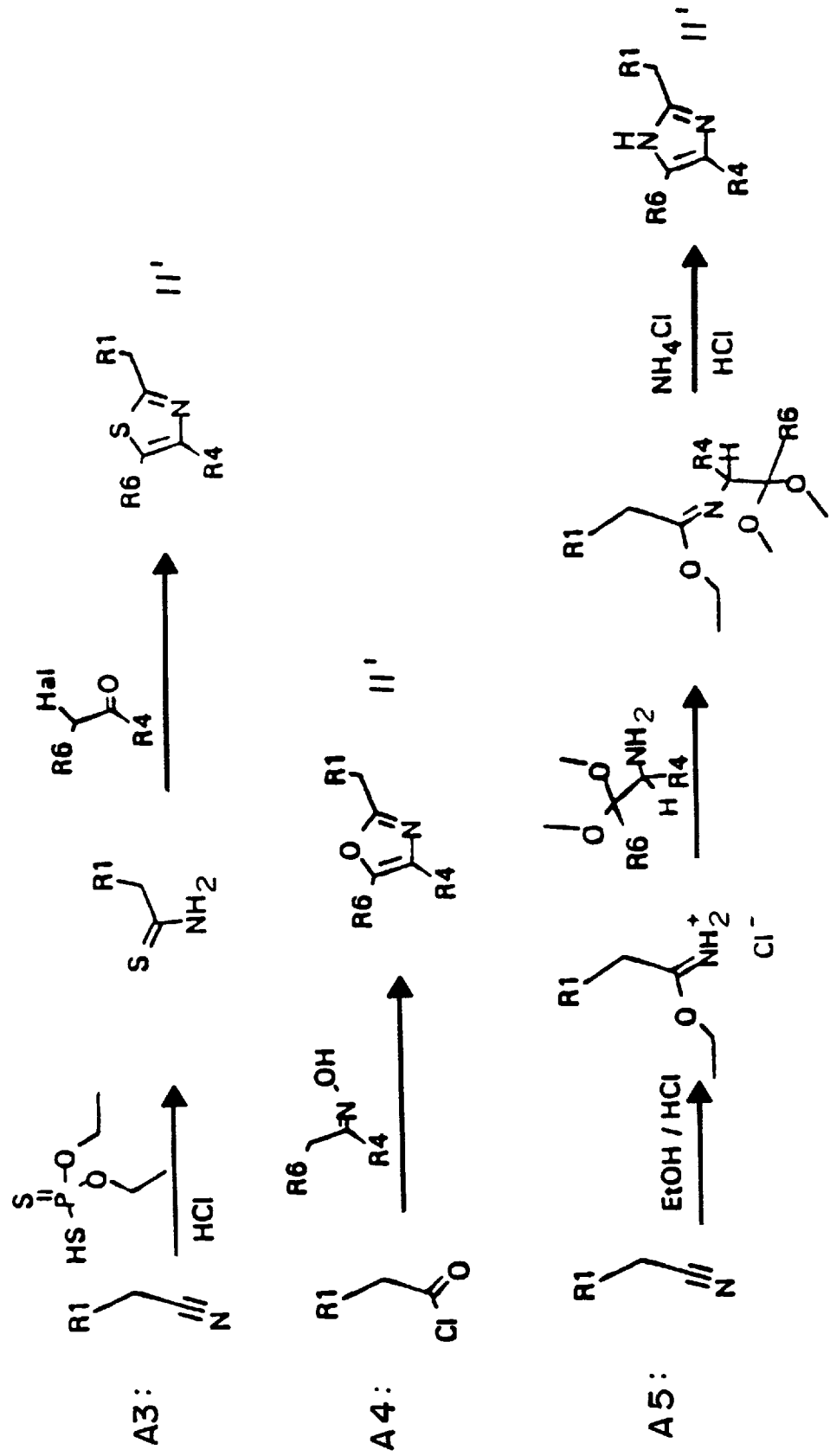
Figure 2:
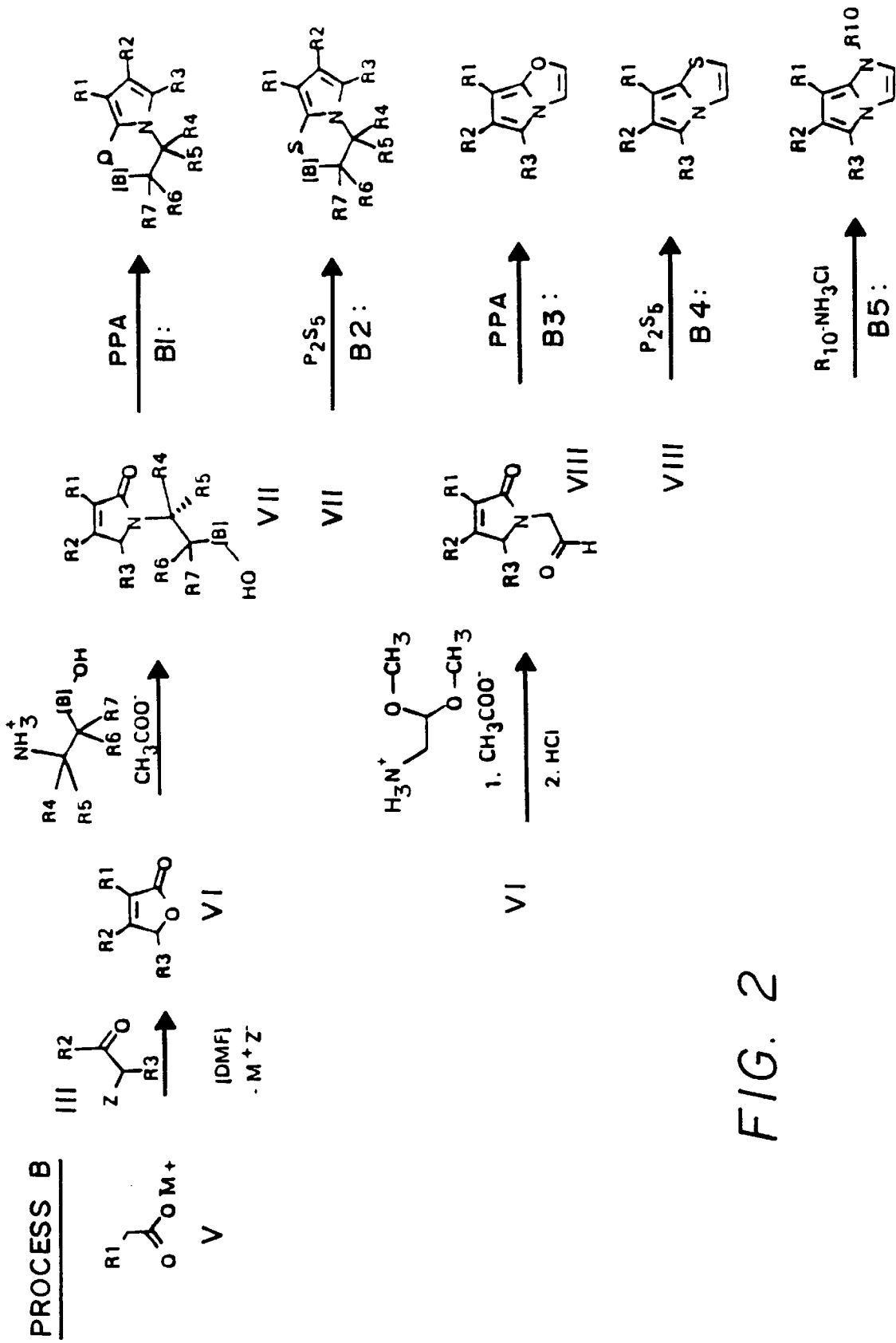

Depending on the condensation reagent used and on the second functional group of the bifunctional amines NH$_2$—CR$^4$R$^5$CR$^6$R$^7$-[B]$_a$-OH or NH$_2$CH$_2$CH(OCH$_3$)$_2$, the cyclization to the anellated heterocycle leads to partially hydrated forms (formula I", FIG. 2: B1/B2) or to dehydrated forms (formula I', FIG. 2: B3, B4, B5).

Figure 3A:
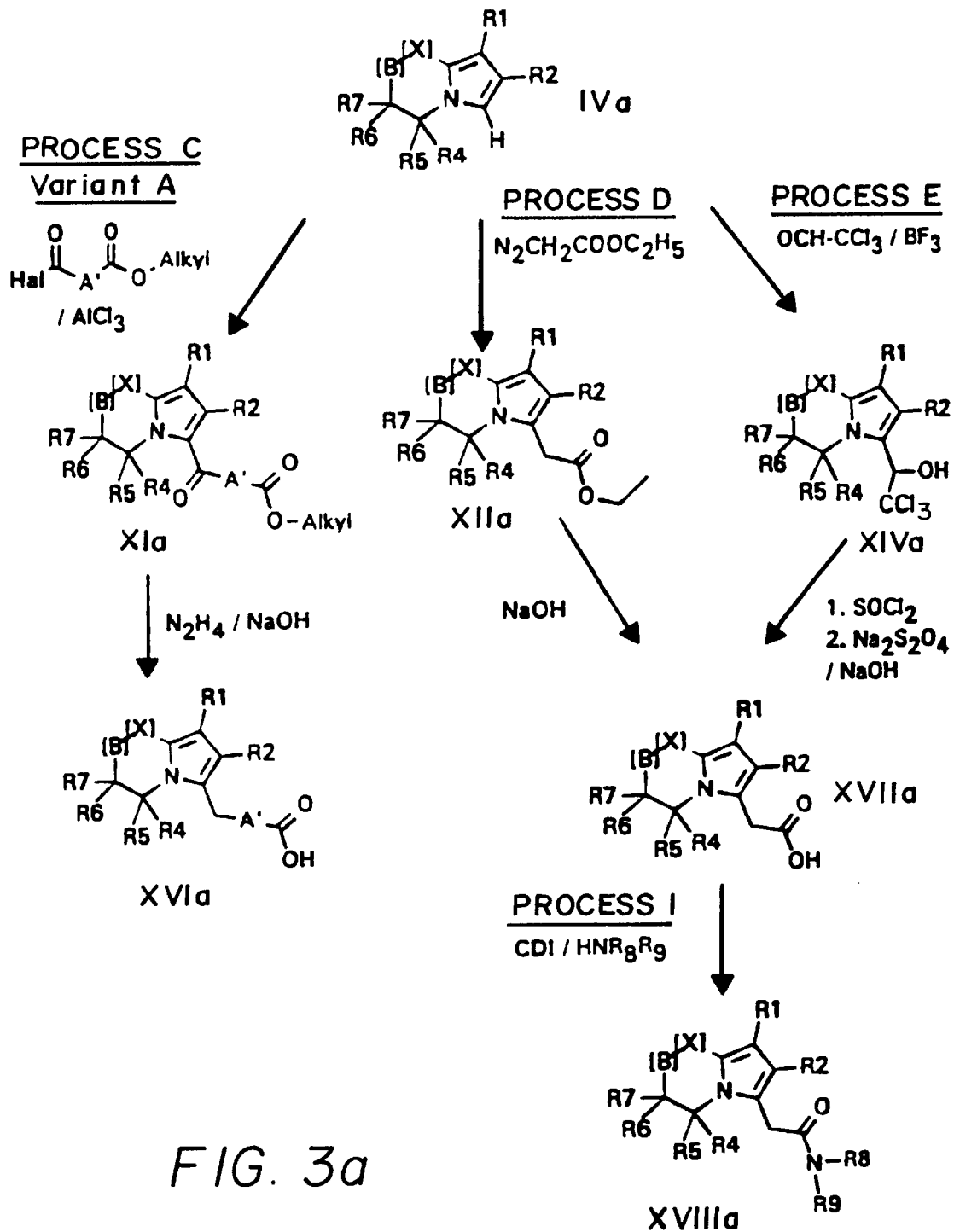

If desired, a different substituent is inserted into the heterocyclic base structure, according to methods known to one skilled in the art. For example, these methods can include:

a) Reaction of a formula IV compound with a carboxylic acid halide HalOC-A'-COO alkyl, in which A' stands for a chemical bond, C$_1$–C$_7$ alkylene or C$_2$–C$_7$ alkenylene and Hal stands for Cl or Br (FIG. 3a, process C/variant A). The formula Ia compound obtained, in which one of the radicals R$^1$, R$^2$, and R$^3$ stands for CO-A'-CO$_2$ alkyl, is then treated with a reagent which is suitable for the reduction of the carbonyl group to a CH$_2$ group, for example hydrazine, NaCNBH$_3$ or zinc amalgam.

The reaction with the carboxylic acid halide is carried out in an inert solvent, e.g. diethyl ether or tetrahydrofuran, optionally in the presence of a catalyst. The reduction with hydrazine is preferably carried out in a high-boiling alcohol, e.g. diethylene glycol. The formula XVI compounds are obtained in this manner.

b) The production of the formula I compounds, in which one of the radicals R$^1$, R$^2$, and R$^3$ stands for A-CONR$^8$R$^9$, is carried out starting from the correspondingly activated derivatives of formula I carboxylic acid, in which one of the radicals R$^1$, R$^2$, or R$^3$ stands for ACO$_2$H, by means of reaction with the corresponding sulfonamide, hydroxylamine, amine, or amide (see FIG. 3a, formula XVIII, A=CH$_2$). Suitable activated carboxylic acid derivatives are known to one skilled in the art, the imidazolide derivative is preferable.

Figure 3B:
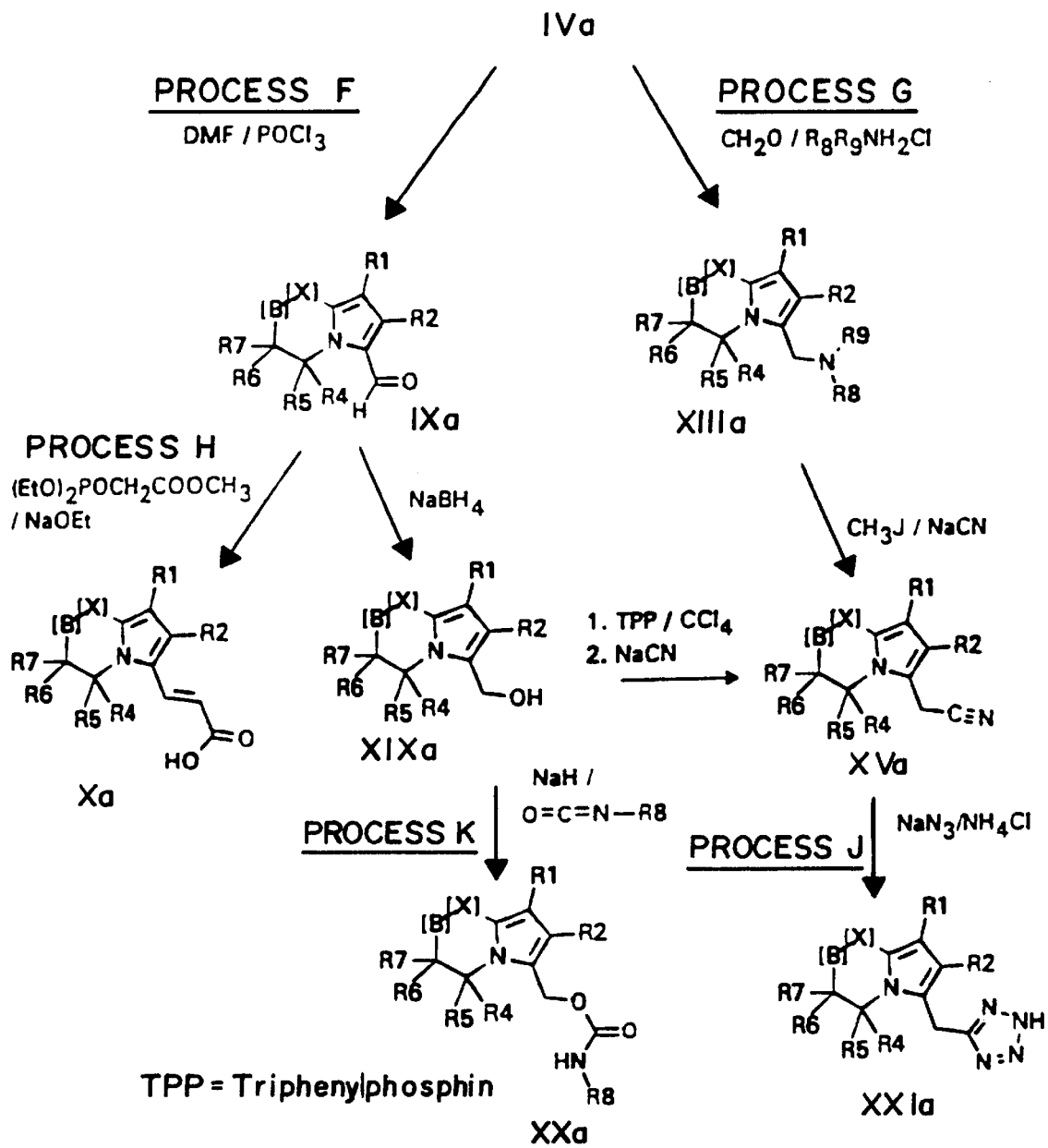
Figure 4:
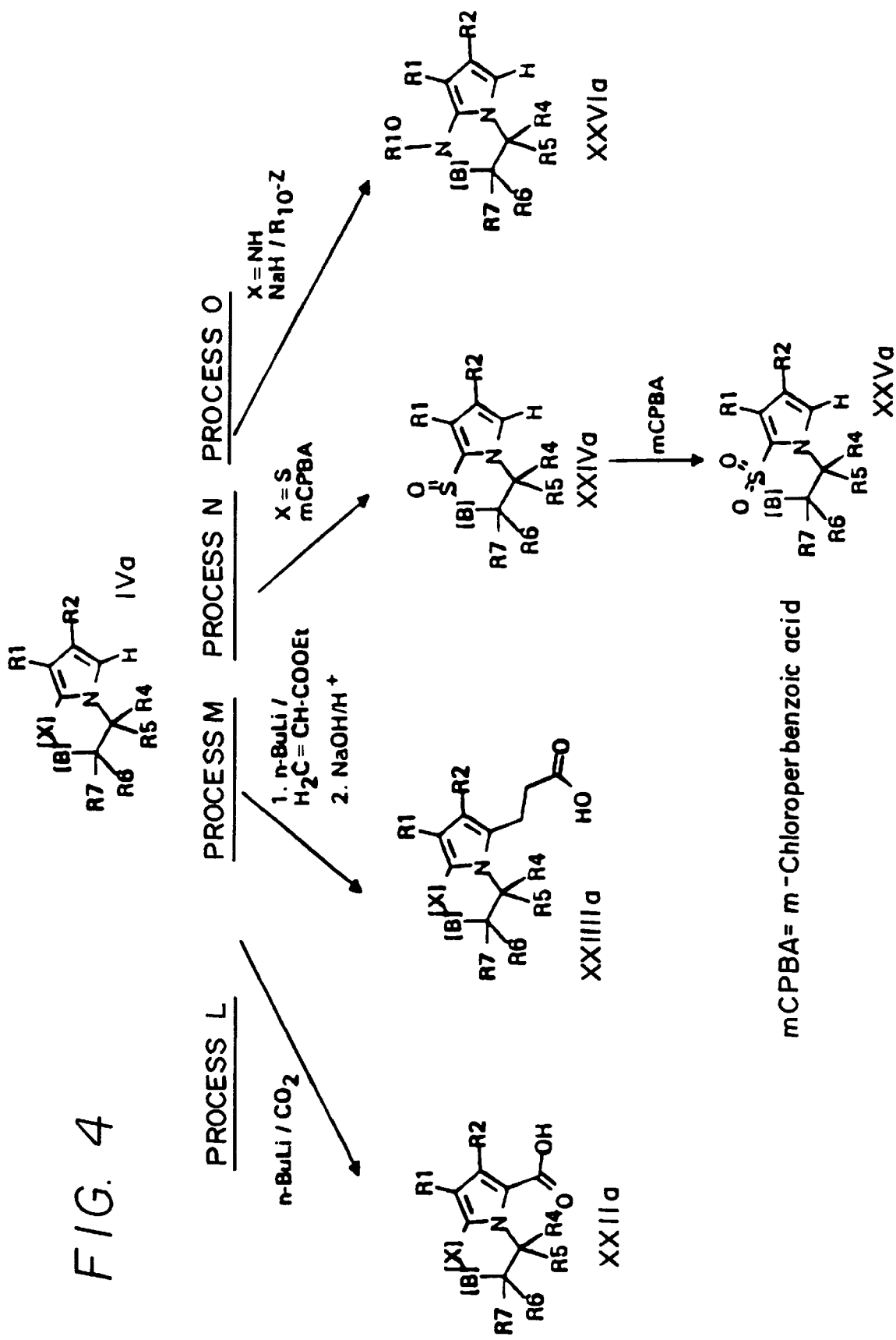
Figure 5A:
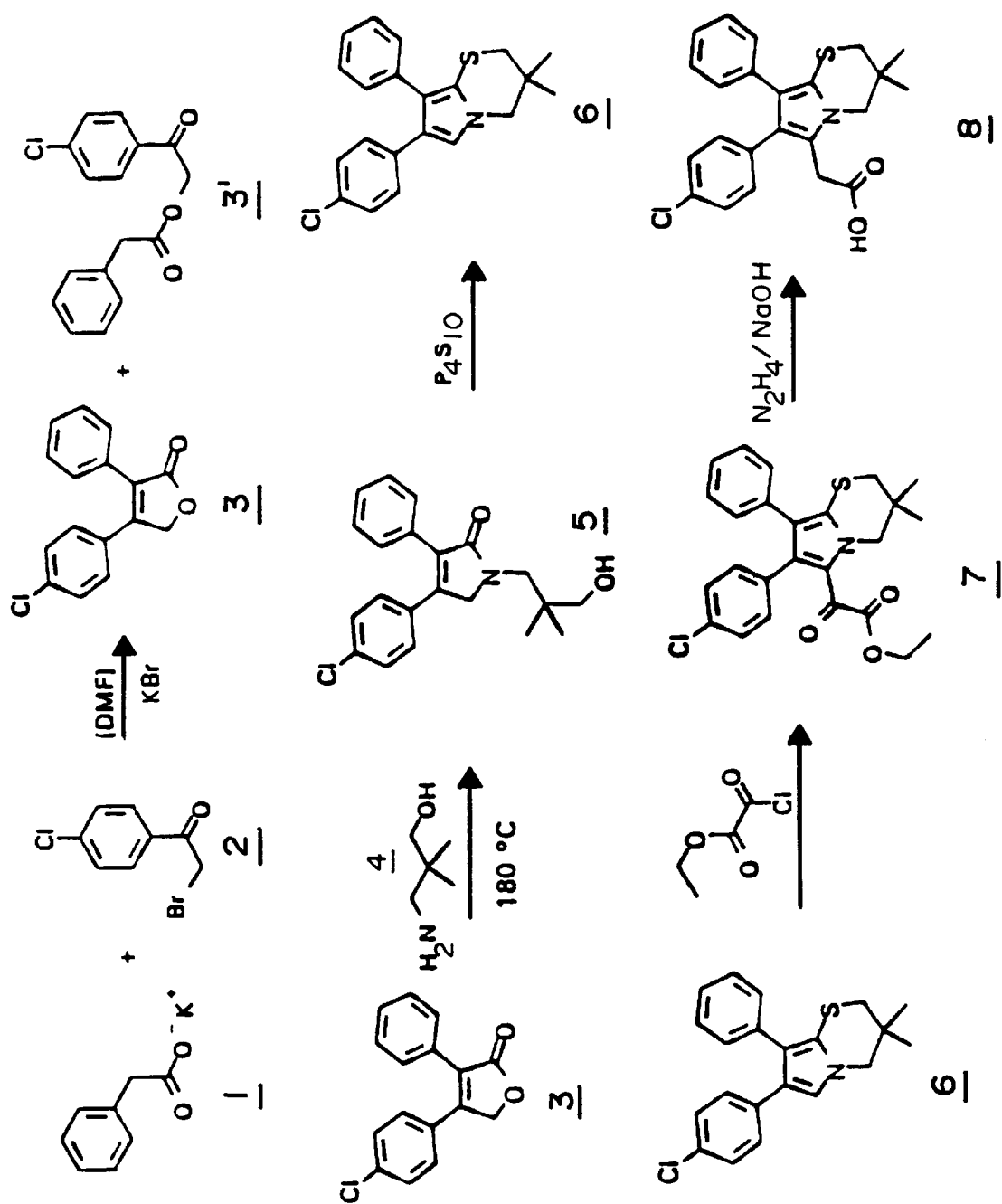
Figure 5B:
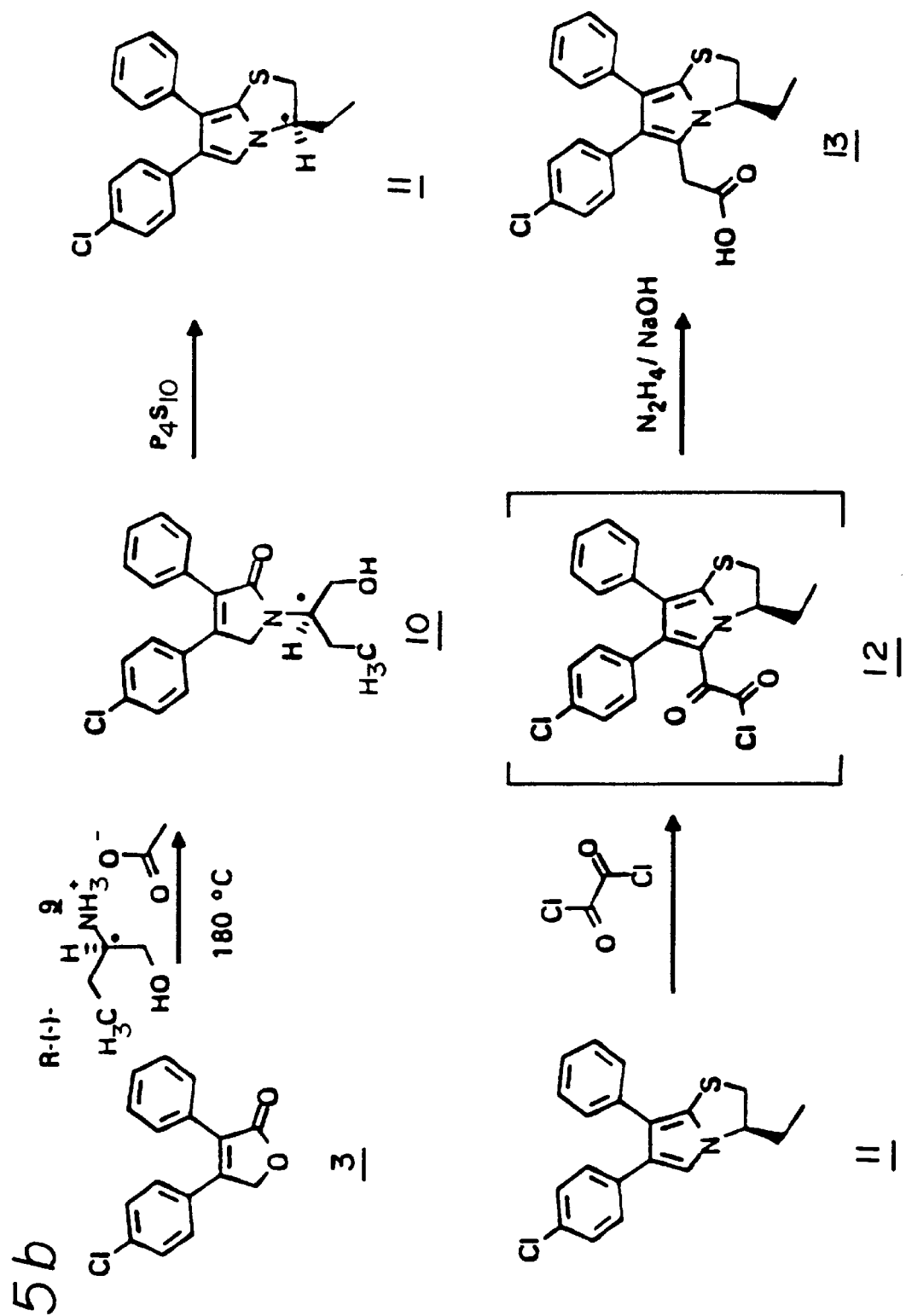

The reaction is carried out in an inert solvent, for example an ether such as diethyl ether or tetrahydrofuran, in the presence of a base, for example sodium hydride. The reaction temperature lies in the range that extends from room temperature to the boiling point of the solvent. The reaction is suitably carried out at room temperature.

c) There are a number of methods available for inserting the particularly preferable group CH$_2$CO$_2$H (see FIGS. 3a, 3b, and 4). The first possibility comprises reacting a formula IV compound with oxalylchloride (FIG. 5b), wherein a formula I compound is obtained, in which one of the radicals R$^1$, R$^2$, and R$^3$ stands for COCO$_2$H. This compound is then treated with a reagent which is suited to the reduction of the ketocarbonyl group, for example hydrazine, HaCNBH$_3$, or zinc amalgam. The reduction with hydrazine is preferable under the conditions of a Wolff-Kishner reduction and in particular the Huang-Minlon variant of it (also see point a) above).

Another possibility comprises reacting a formula IV compound with a diazoethanoic acid alkyl ester producing a formula Ic compound in which one of the radicals $R^1$, $R^2$, and $R^3$ stands for $CH_2COO$ alkyl. If so desired, this compound is then subjected to ester cleavage into the corresponding free carboxylic acid. (FIG. 3a, XVII).

The reaction with the diazoethanoic acid is carried out in an inert solvent, for example toluene or xylene, in the presence of copper powder or complex copper(I) salts or copper(II) salts. The reaction is carried out at an increased temperature, suitably at the boiling temperature of the solvent used.

A further possibility comprises the reaction of a formula IV compound with chloral producing a formula XIV compound and treatment of the activated compound with a dithionite, for example sodium dithionite or with a sulfinate, e.g. hydroxymethane sulfinic acid sodium salt; see FIG. 3, process E.

d) The insertion of a formyl group or methylol group into the pyrrole ring is carried out through the reaction of a formula IV compound with phosphorus oxychloride/dimethyl formamide (see FIG. 3b). The reaction is carried out in an inert solvent, for example benzene, toluene, or xylene, at an increased temperature, suitably at the boiling point of the solvent used. A formula IX compound is obtained, in which one of the radicals $R^1$, $R^2$, and $R^3$ stands for CHO. This formyl group can then be reduced in a usual way, for example with lithium aluminum hydride in an inert solvent, for example tetrahydrofuran, or with sodium hydroboron in aqueous alkaline solution, forming the corresponding hydroxymethyl compound XIX (FIG. 3b). This can then be used as a starting material for further reactions for the insertion of the desired groups (process K, J; FIG. 3b).

Furthermore, the formyl group in a Wittig reaction carried out under normal conditions can be transformed into a corresponding alkenylene group producing the compound X (see compound X in FIG. 3b). If so desired, this can in turn be hydrated in a usual way, forming the corresponding alkylene compound (XXIII, FIG. 4).

e) Reaction of a formula IV compound with an anhydride with the formula:

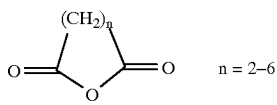

n = 2–6 produces the corresponding formula I ketocarboxylic acids, in which one of the radicals $R^1$, $R^2$, and $R^3$ stands for $CO(CH_2)_nCO_2H$. With the reagent already mentioned, the ketocarbonyl group can be reduced to a $CH_2$ group (see FIGS. 3, 3a, XI–XVI).

f) A carboxyl group can be inserted by the reaction of a formula IV compound with n-butyl lithium in an inert solvent at a low temperature and by the subsequent routing of $CO_2$ gas through the solution of the lithium organic compound formed; formula XXII compounds are obtained (see process L, FIG. 4).

g) Esters can be produced from carboxylic acids in a customary fashion by esterification and carboxylic acids can be produced from esters in a normal manner by ester cleavage.

The production of other compounds according to the invention is carried out analogously (FIGS. 3a, 3b, 4), optionally through further reactions which are known to one skilled in the art.

The compounds according to the invention have proved to be potent cyclooxygenase and/or lipoxygenase inhibitors. They are distinguished by a strong analgesic effect and by a uniform inhibiting action on the enzymes cyclooxygenase (CO) and lipoxygenase (LO) ($IC_{50}LO/IC_{50}CO\sim 1$). They can therefore be used in the treatment of diseases which are associated with a change in arachidonic acid metabolism. In particular, this pertains to diseases of the rheumatoid variety and the prevention of allergically induced diseases. The compounds according to the invention consequently represent effective anti-inflammatory drugs, analgesics, antipyretics, antiallergics, and are effective against bronchial constriction and can therefore be used for thrombosis prophylaxis and for the prophylaxis of anaphylactic shock as well as for the treatment of dermatological diseases such as psoriasis, urticaria, acute and chronic exanthemas of allergic and non-allergic genesis. Moreover, they are usable to treat hypercholesteremia.

The compounds according to the invention can be administered either as individual therapeutic agents or as mixtures with other therapeutic agents: They can be administered as is, but in general, they are administered in the form of pharmaceuticals, that is, as mixtures of agents with suitable pharmaceutical vehicles or diluents. The compounds or agents can be administered orally or parenterally, preferably, though, they are given in oral dosage forms.

The type of pharmaceutical and the type of pharmaceutical vehicle or diluent depend on the desired type of administration. Oral agents can be in tablet or capsule form and can contain conventional excipients such as binders (e.g. syrup, acacia, gelatine, sorbitol, tragacanth, or polyvinyl pyrrolidone), fillers (e.g. lactose, sugar, cornstarch, calcium phosphate, sorbitol, or glycine), lubricants (e.g. magnesium stearate, talcum, polyethylene glycol, or silicon dioxide), disintegrating agents (e.g. starch), or wetting agents (e.g. sodium lauryl sulfate). Oral fluid preparations can be in the form of aqueous or oleaginous suspensions, solutions, emulsions, syrups, elixirs, or sprays, etc. or can be in the form of dry powder for reconstitution in water or another suitable vehicle. Fluid preparations of this kind can contain conventional additives, for example suspension agents, flavorings, diluents, or emulsifying agents. For parenteral administration, solutions or suspensions can be used with standard pharmaceutical vehicles.

The compounds or agents according to the invention can be administered to a mammal (human and animal) in doses of approximately 0.5 mg to approximately 100 mg per kg of body weight per day. They can be administered in a single dose or in a number of doses.

The efficacy of the compounds according to the invention can be determined from the inhibition of 5-lipoxygenase or cyclooxygenase. Experiments have be carried out according to Dannhardt et al., J. Pharm. Pharmacol. 1992, 44: 419–424.

The spectrum of efficacy of the compounds was also investigated using the following tests:

1) Phenylquinone writhing test in the mouse p.o., S. Irwin, Psychopharmacologia, 13:222–257, 1968;

2) Formalin analgesia test in the mouse p.o., B. Rubin et al., Endocrinol., 49:429–439, 1951;

3) Inhibition of arachidonic acid-induced platelet aggregation, V. Bertele et al., Science 220:517–519 (1983);

4) Inhibiting inflammation in rat paw edema, C. A. Winter et al., Proc. Exper. Biol. Med., 111:544–547 (1962);

5) Tracheal relaxation in the guinea pig, F. P. Luduena et al., Arch. Int. Pharmacodyn., 111:392–400, 1957;

6) Cholesterol-reducing action in the mouse, C. E. Day et al., Atherosclerosis Drug Discovery, Ed. Charles E. Day, Plenum Publishing Corp., New York, 1976, 231–249.

The results are given in the following Table 1:

TABLE 1

| | | Pharmacological Effect | | | | | |
|---|---|---|---|---|---|---|---|
| | | Test Models | | | | | |
| Compound[1] | IC50 LO/CO | 1 | 2 | 3 | 4 | 5 | 6 |
| 1 | $4 \times 10^{-7}/2 \times 10^{-7}$ | x | x | x | | x | |
| 8 | | | x | x | | x | |
| 9 | | x | x | x | | | |
| 10 | | | | x | | | x |
| 11 | | | x | x | x | | |
| 12 | | | | x | | | x |
| 6 | $4 \times 10^{-8}/x\ 8 \cdot 10^{-7}$ | | | | | | |
| 14 | | | | | | | x |

[1]Number of the Example

It was found that the compound of Example 1 ($R_2$=5-chloro-2-thienyl), compared with the corresponding 4-chlorophenyl derivative in vivo, is 10 times more analgesically effective. In the formalin analgesia model of the mouse, an MED of 10 md/kg results, as compared with 100 mg/kg.

The following examples explain the invention. All temperature data is uncorrected. The IR spectra of crystalline substances were picked up from a KBr compact and the oily substances from a film. Unless otherwise noted, the NMR spectra are 200 MHz spectra, picked up in $CDCl_3$ with tetramethylsilane (TMS) as an internal standard. The IR spectra are indicated in $cm^{-1}$ and the NMR spectra are indicated in δ(ppm).

EXAMPLES

General Recipe for Preparing Heteroaryl-substituted [a]- or [1,2]-anellated pyrroles (pyrrolo[1,2-a] pyrroles=pyrrolizines, pyrrolo[1,2-a]pyridines= indolizines, pyrrolo[1,2-a]azepines)

To a solution of 20 mmol omega-bromacetyl compound in 100 ml methylene chloride, 20 mmol of the corresponding cyclic imine derivative in 50 ml of methylene chloride is added quickly drop by drop and stirred for 4 h at room temperature with the exclusion of moisture. Next, 30 ml of 5% aqueous $NaHCO_3$ solution is added, and the mixture is stirred intensively for another 4 h. After the addition of 200 ml of water, the organic phase is separated off, dried over $Na_2SO_4$, and evaporated at reduced pressure. The residue is made to crystallize with methanol, and optionally recrystallized from methanol.

General Recipe for Preparing Heteroaryl-substituted [a]- or [1,2]-anellated pyrrol-5-yl-oxoacetic acids To a solution of 1.4 mmol oxalic acid ethyl ester chloride in 20 ml of dry methylene chloride, 1.3 mmol of correspondingly substituted anellated pyrrole, dissolved in 20 ml of dry methylene chloride, is added drop by drop while stirring, and stirring is continued for 20 min. After 40 ml of water is carefully added, the organic phase is separated out and dried over $Na_2SO_4$. The residue remaining after the solvent has been extracted is suspended in 20 ml diisopropyl ether aspirated off, and rewashed two more times with 5 ml of diisopropyl ether each time.

General Recipe for Preparing Heteroaryl-substituted [a]- or [1,2]-anellated pyrrol-5-yl-acetic acids 2 mmol of the corresponding oxoester derivative are mixed with 2 ml of diethylene glycol and 1.5 ml of 80% hydrazine derivative and stirred for 30 min at 60° C. Next, 2.1 g of potassium hydroxide are added, and the reaction mixture is heated while stirring for 2 h to 140° C.

The still-warm mixture is added to 20 ml of ice water and adjusted with dilute phosphoric acid to pH=3–4; the raw product settled out as a solid. This is aspirated, rewashed several times with water, dried in a vacuum, and then washed several times with a little diisopropyl ether.

General Recipe for Preparing N-sulfonylated [a]- or [1,2]-anellated heteroarylpyrrolcarboxylic acid amides Mixture A:

2.6 mmol of the applicable pyrrolcarboxylic acid are stirred with 5 mmol of carbonyl diimidazole in 25 ml dry tetrahydrofuran for 1 h at room temperature.

Mixture B:

3 mmol of the correspondingly substituted sulfonamide are dissolved in 20 ml dry tetrahydrofuran in an argon atmosphere, mixed with 3.3 mmol sodium hydride (mineral oil suspension), and stirred for 1 h at room temperature.

Mixture B is added in an argon atmosphere to mixture A and stirred for 40 h. The suspension is poured onto 40 ml of ice water, adjusted with dilute phosphoric acid to pH=4, and extracted multiple times with diethyl ether. After drying of the organic phase over $Na_2SO_4$ and extraction of the solvent, the remaining residue is recrystalized from isopropanol.

The synthesis of 5,7-(hetero)aryl-substituted pyrrolizines was done as in EP-A 397 175.

The corresponding bromaldehydes were prepared, as in Riehl, J. J., C. R. Hebd. Seance, Acad. Sci. Ser. C (1957), 245:1321–1322, from the following:

2-Pyridylacetaldehyde Leaver et al., J. Chem. Soc. [1963] 6053.
4-Pyridylacetaldehyde Julia et al., J. Chem. Soc. Perkin Trans. 1 [1978] 1646–1650.
2-Pyridylacetaldehyde Hey, Williams, J. Chem. Soc. [1950] 1678.
2-Quinolylacetaldehyde Analogous to Leaver et al. method (see above) for 2-pyridylacetaldehyde
3-Indolylacetaldehyde Plieninger, Weist; Chem. Ber. 89, 2783 [1956] Chem. Ber. 88, 1956 [1955]
2-N-Methylpyrrolacetaldehyde Hess, Merck, Uibig, Chem. Ber. 48, 1894 [1915]
5-Chloro-2-thienylacetaldehyde Mason, Nord.; J. Org. Chem. 16 [1951] 1869–1871
2-Furanylacetaldehyde Reichstein, Chem. Ber. 63 [1930] 749–753

The insertion of the A-Y radicals into position 6 was again done as in EP-A 397 175.

The intermediate compounds and final compounds obtained are shown in the following Tables 2 and 4. Their physical data follow in Tables 3 and 5, respectively.

TABLE 2

I'/I"

[Structure: bicyclic compound with R1, R2, R3, R4, R5, R6, R7 substituents and X in ring]

Reference Examples

| Reference Example # | R¹ | R² | R³ | R⁴ | R⁵ | R⁶ | R⁷ | X |
|---|---|---|---|---|---|---|---|---|
| 1 | Ph | 5-Cl-2-thienyl | H | H | H | $CH_3$ | $CH_3$ | $CH_2$ |
| 2 | Ph | 5-Cl-2-thienyl | $COCO_2Et$ | H | H | $CH_3$ | $CH_3$ | $CH_2$ |
| 3 | Ph | 3-thienyl | H | H | H | $CH_3$ | $CH_3$ | $CH_2$ |
| 4 | Ph | 3-thienyl | $COCO_2Et$ | H | H | $CH_3$ | $CH_3$ | $CH_2$ |
| 5 | Ph | 2-benzofuranyl | H | H | H | $CH_3$ | $CH_3$ | $CH_2$ |
| 6 | Ph | 2-benzofuranyl | $COCO_2Et$ | H | H | $CH_3$ | $CH_3$ | $CH_2$ |
| 7 | Ph | 2-furanyl | H | H | H | $CH_3$ | $CH_3$ | $CH_2$ |
| 8 | Ph | 2-furanyl | $COCO_2Et$ | H | H | $CH_3$ | $CH_3$ | $CH_2$ |
| 9 | 5-Cl-2-thienyl | 4-Cl-Ph | H | H | H | $CH_3$ | $CH_3$ | $CH_2$ |
| 10 | 5-Cl-2-thienyl | 4-Cl-Ph | $COCO_2Et$ | H | H | $CH_3$ | $CH_3$ | $CH_2$ |
| 11 | Ph | 2-Chinolinyl | H | H | H | $CH_3$ | $CH_3$ | $CH_2$ |
| 12 | Ph | 2-Chinolinyl | $COCO_2Et$ | H | H | $CH_3$ | $CH_3$ | $CH_2$ |
| 13 | Ph | 4-pyridyl | H | H | H | $CH_3$ | $CH_3$ | $CH_2$ |
| 14 | Ph | 4-pyridyl | $COCO_2Et$ | H | H | $CH_3$ | $CH_3$ | $CH_2$ |
| 15 | Ph | 5-Cl-2-thienyl | H | H | H | $CH_2CH_3$ | $CH_2CH_3$ | $CH_2$ |
| 16 | Ph | 5-Cl-2-thienyl | $COCO_2Et$ | H | H | $CH_2CH_3$ | $CH_2CH_3$ | $CH_2$ |
| 17 | Ph | H | 5-Cl-2thienyl | H | H | H | H | $CH_2$ |
| 18 | Ph | $CO(CH_2)_3CO_2H$ | 5-Cl-2-thienyl | H | H | H | H | $CH_2$ |
| 19[1)] | Ph | 5-Cl-2-thienyl | H | $CH_3$ | — | H | — | S |
| 20[1)] | Ph | 5-Cl-2-thienyl | $CH_2CO_2Et$ | $CH_3$ | — | H | — | S |

[1)]Compound of formula I'

TABLE 3

| Compound of Reference Example # | |
|---|---|
| 1 | B.P.: oil<br>IR: 2950, 1656, 1596, 1444, 1414, 1382, 792, 759, 697<br>NMR: 7.29–7.17(m, 5H, arom); 6.71(s, 1H, N—CH—); 6.70 (AB, J = 3.5, =CH—); 6.49(AB, J = 3.5, =CH—); 3.72(s, 2H, —CH₂—N); 2.75(s, 2H, —CH₂—); 1.27(s, 6H, —CH₃) |
| 2 | B.P.: 133.0° C.<br>IR: 2955, 1736, 1619, 1467, 1426, 1373, 1241, 1179, 1049, 701<br>NMR: 7.26–7.10(m, 5H, arom); 6.82(AB, J = 3.7, —CH=); 6.77 (AB, J = 3.7, —CH=); 4.22(s, 2H, —CH₂N—); 3.87(q, 2H, J = 7.0, ethyl); 2.82(s, 2H, —CH₂—); 7.31(s, 6H, —CH₂); 1.19(t, 3H, J = 7.0, ethyl) |
| 3 | B.P.: oil<br>IR: 2945, 1597, 1551, 1460, 1416, 1363, 1156, 757, 696<br>NMR: 7.27–7.17(m, 5H, arom.); 6.97(s, 1H, ); 6.95(s, 1H,); 6.72(s, 1H, =CH—N—); 3.73(s, 2H, —CH₂N—); 2.78(s, 2H, pyr.); 1.28(s, 6H, —CH₃) |
| 4 | B.P. 136.4° C.<br>IR: 2950, 1732, 1609, 1450, 1420, 1249, 1132, 1062, 743<br>NMR: 7.26–6.88(m, 8H, arom = ABX-thienyl); 4.23(s, 2H, —CH₂—N—); 3.75(q, 2H, J = 7.0, ethyl); 2.85(s, 2H, pyr); 1.32(s, 6H, —CH₃); 1.12(t, 3H, J = 7.0) |
| 5 | B.P.: 145.2° C.<br>IR: 2945, 1601, 1462, 1276, 1249, 1162, 970, 790, 740, 698<br>NMR: 7.4–7.11(m, 10H, arom.benzofuran); 6.31 (d, 1H, =CH—N, J = 0.76Hz); 3.77(s, 2H, —CH₂—N—); 2.74(s, 2H, —CH₂—); 1.28(s, 6H, —CH₃) |
| 6 | B.P.: 161° C.<br>IR: 2950, 1625, 1739, 1451, 1423, 1370, 1306, 1241, 1199, 1060<br>NMR: 7.53–7.17(m, 9H, arom, benzofuran); 6.58(d, 1H, J = 0.75Hz; 4.23(s, 2H, —CH₂—N); 3.65(q, 2H, J = 7.2Hz, ethyl); 2.83 (s, 2H, —CH₂—)<br>1.33(s, 6H, —CH₃); 0.98(t, 3H, J = 7.2Hz, ethyl) |

TABLE 3-continued

| Compound of Reference Example # | |
|---|---|
| 7 | B.P. 107.7<br>IR: 2940, 1600, 1478, 1368, 1176, 1008, 968, 753, 721, 698<br>NMR: 7.33–7.17(m, 6H, arom, =CH—O); 6.88<br>(s, 1H =CH—N—); 6.30(dd, 1H, J = 1.8Hz); 6.01(d, 1H, J = 3.2Hz);<br>3.73(s, 2H, —CH$_2$—N—), 2.4(s, 2H, —CH$_2$— pyr.)); 1.29(s, 6H, —CH$_3$) |
| 8 | B.P. 129° C.<br>IR: 2975, 1719, 1616, 1443, 1262, 1181, 1062, 757, 692<br>NMR: 7.43–7.10(m, 6H, arom = CH—O));<br>6.41(dd, 1H, J = 1.9,); 6.23(d, 1H, J = 3.2); 4.21(s, 2H, —CH$_2$N—);<br>3.95(q, 2H, J = 7.1, ethyl); 2.84(s, 2H, CH$_2$pyr); 1.32(s, 6H, —CH$_3$);<br>1.15(t, 3H, J = 7.1, ethyl) |
| 9 | B.P. 83° C. |
| 10 | B.P. 183° C. |
| 11 | B.P.: oil<br>NMR: 8.30–8.05(m, 3H, Chinolinyl); 7.95–7.7(m, 2H);<br>7.65–7.25(m, 6H,) 6.95(s, 1H, Pyrrol); 3.88(s, 2H, CH$_2$);<br>2.94(s; 2H, CH$_2$); 1.31(s, 6H, 2CH$_3$) |
| 12 | B.P. 153° C.<br>IR: 1740<br>NMR: 8.35–8.15(m, 3H, Chinolin), 8.0–7.3(m, 8H,<br>Phenyl + 3HCh(inolin); 4.87(s; 2H, CH$_2$), 312(q, 2H, OCH$_2$—CH$_3$);<br>2.95(s; 2H, CH$_2$); 1.36(s 6H, 2CH$_3$); 0.79(t, 3H, CH$_2$—CH$_3$) |
| 13 | B.P.: oil<br>NMR: 8.8–8.55(m, 2H, AA', Pyridyl); 7.8–7.3(m, 7H,<br>BB' Pyridyl + Ar) 6.8(s, 1H, Pyrrol-H); 3.82(s, 2H, CH$_2$) 2.85(s, 2H,<br>CH$_2$); 1.30(6H, s, 2CH$_3$) |
| 14 | B.P. 152° C.<br>IR: 1736 (C=O)<br>NMR: 0.8(t, 3H, J = 6.7Hz, CH$_2$—CH$_3$), 1.37(s, 6H, 2CH$_3$);<br>2.95(s, 2H, CH$_2$), 3.12(q, 2H, O—CH$_2$—CH$_3$); 4.36(s, 2H, CH$_2$);<br>9.05–8.75(m, 2H, AA'); 8.0–7.1(m, 7H, BB' + Ar) |
| 15 | B.P. 80.3° C.<br>IR: 2995, 1550, 1447, 1380, 1157, 1062, 986, 786, 758, 694<br>NMR: 7.30–7.15(m, 5H, arom); 6.68(d, AB, 1H, J = 4.0, thienyl); 6.47<br>(d, AB, 1H, thienyl) (6.67(s, 1H, —N—CH=); 3.74(s, 2H, —CH$_2$—N);<br>2.73(s, 2H, —CH$_2$pyr); |
| 16 | B.P.: 126.8<br>IR: C=O; 1750, 1629<br>NMR: 7.31–7.09(m, 5H, arom); 6.81 + 6.76(AB, 2H, J = 3.7,<br>—CH=CH—) 4.23(s, 2H, —CH$_2$—N—); 3.87(q, 2H, J = 7.2, ethylester);<br>2.79<br>(s, 2H, CH$_2$) |
| 17 | B.P.: 142° C.<br>NMR: 7.3–7.1(m, 5H, Arn); 6.70(H$_A$, JS$_{AB}$ = 3.3), 6.49(H$_B$;<br>J$_{AB}$ = 3.39) 6.66(s, 1H, Pyrrol H); 4.07(t, 2H; CH$_2$), 3,04 (t,,2H;<br>CH$_2$), 2.60(q, 2H, CH$_2$) |
| 18 | B.P. 126° C.<br>IR: 1660, 1706, (C=O)<br>NMR: 8.7–8.5(2H, Ar); 8.5–8.35(3H; Ar); 6.82(H$_A$, J$_{AB}$ = 3.76Hz);<br>6.76(H$_B$, J$_{AB}$ = 3.75Hz); 5.08(t, 2H, CH$_2$); 4.14(t, 2H, CH$_2$);<br>3.67(quint.. 2H, CH$_2$); 3.53(t, 2H, CH$_2$); 3.33(t, 2H, CH$_2$); 2.95<br>(quint.. 2H, CH$_2$). |
| 19 | NMR: 7.24–7.06(m, 5H, Ar); 7.16(s, 1H); 6.80, 6.62(AB, J =<br>3.8Hz, Thiophen-H); 6.31(9.1H, J = 0.8Hz); 2.40(d, 3H, J =<br>0.8Hz) |
| 20 | NMR: 7.26–7.03(m, 5H, Ar); 6.80, 6.62(AB, J = 3.8Hz, Thiphen-<br>H); 6.30(q, 1H, J = 0.8Hz); 3.51(s, 2H, CH$_2$); 2.62q, 2H,<br>6.8Hz); 2.38(d, 3H, 0.8Hz); 1.12(t, 3H, J = 6.8Hz) |

TABLE 4

Structure: pyrrole-fused ring with substituents R¹, R², R³, R⁴, R⁵, R⁶, R⁷, X, [B]ₐ; [B] = CH₂

| Nr. | R$^1$ | R$^2$ | R$^3$ | R$^4$ | R$^5$ | R$^6$ | R$^7$ | X | a |
|---|---|---|---|---|---|---|---|---|---|
| 1 | Ph | 5-Cl-2-thienyl | CH$_2$—CO$_2$H | H | H | CH$_3$ | CH$_3$ | CH$_2$ | 0 |
| 2 | Ph | 3-thienyl | CH$_2$CO$_2$H | H | H | CH$_3$ | CH$_3$ | CH$_2$ | 0 |
| 3 | Ph | 2-benzofuranyl | CH$_2$—CO$_2$H | H | H | CH$_3$ | CH$_3$ | CH$_2$ | 0 |
| 4 | Ph | 2-furanyl | CH$_2$—CO$_2$H | H | H | CH$_3$ | CH$_3$ | CH$_2$ | 0 |
| 5 | 5-Cl-2-thienyl | 4-Cl-ph | CH$_2$CO$_2$H | H | H | CH$_3$ | CH$_3$ | CH$_2$ | 0 |
| 6 | Ph | 2-chinolinyl | CH$_2$—CO$_2$H | H | H | CH$_3$ | CH$_3$ | CH$_2$ | 0 |
| 7 | Ph | 4-pyridyl | CH$_2$—CO$_2$H | H | H | CH$_3$ | CH$_3$ | CH$_2$ | 0 |
| 8 | Ph | 5-Cl-2-thienyl | CH$_2$—CO$_2$H | H | H | CH$_2$CH$_3$ | CH$_2$CH$_3$ | CH$_2$ | 0 |
| 9 | Ph | 5-Cl-2-thienyl | CH$_2$—CONHSO$_2$CH$_3$ | H | H | CH$_2$CH$_3$ | CH$_2$CH$_3$ | CH$_2$ | 0 |
| 10 | Ph | 5-Cl-2-thienyl | CH$_2$—CONHTosyl | H | H | CH$_2$CH$_3$ | CH$_2$CH$_3$ | CH$_2$ | 0 |
| 11 | Ph | 5-Cl-2-thienyl | CH$_2$—CONHSO$_2$CH$_3$ | H | H | CH$_3$ | CH$_3$ | CH$_2$ | 0 |
| 12 | Ph | 5-Cl-2-thienyl | CH$_2$—CONHTosyl | H | H | CH$_3$ | CH$_3$ | CH$_2$ | 0 |
| 13 | Ph | 5-Cl-2-thienyl | (CH$_2$)$_2$—CO$_2$H | H | H | CH$_3$ | CH$_3$ | CH$_2$ | 0 |
| 14 | Ph | (CH$_2$)$_4$CO$_2$H | 5-Cl-2-thienyl | H | H | H | H | CH$_2$ | 0 |
| 15 | Ph | 5-Cl-2-thienyl | (CH$_2$)$_2$—CO$_2$H | H | H | H | H | CH$_2$ | 0 |
| 16 | Ph | 5-Cl-2-thienyl | CH$_2$—CO$_2$H | CH$_3$ | — | H | — | S | 0 |
| 17 | Ph | 5-Cl-2-thienyl | CH$_2$—CONHSO$_2$CH$_3$ | CH$_3$ | — | H | — | S | 0 |

TABLE 5

| Compound of Example # | |
|---|---|
| 1 | B.P.: 164° C.<br>IR: 2920, 1706, 1599, 1441, 1417, 1250, 1222, 1056, 802. 694<br>NMR: 7.24–7.12(m, 5H, arom.); 6.80, 6.62(AB, 3.8Hz, Thiophen), 3.73(s, 2H, —CH$_2$N—); 3.67(s, 2H, —CH$_2$—C=O); 2.83(s, 2H, —CH$_2$—); 1.28(s, 6H, —CH$_3$) |
| 2 | B.P.: 157.2° C.<br>IR: : 2950, 1700, 1598, 1447, 1412, 1307, 1270, 1224, 790, 685<br>NMR: 7.26–7.08(m, 7H, arom. ABX-thienyl); 6.83(dd, ABX, 1H, Thienyl); 3.76(s, 2H, —CH$_2$—N—); 3.64(s, 2H, —CH$_2$—CO—); 2.85(s, 2H, —CH$_2$—); 1.30(0.6H, —CH$_3$) |
| 3 | B.P.: 153.6° C.<br>IR: 2950, 1707, 1600, 1451, 1416, 1251, 1217, 1163, 746, 696<br>NMR: 7.48–7.15(m, 9H, arom. benzofuran); 6.43(d, 1H, J = 0.6Hz CH=C—O); 3.89(s, 2H, —CH$_2$—N—); 3.75(s, 2H, —CH$_2$—C=O); 2.81(s, 2H, —CH$_2$-pyr); 1.29(s, 6H, —CH$_3$) |
| 4 | B.P. 164° C.<br>IR: 3425, 2950, 1702, 1600, 1446, 1289, 1174, 1008, 758, 697<br>NMR: 7.37–7.10(m, 6H, arom + =CH—O—); 6.37(dd, 1H, J = 1.9); 6.13 (d', 1H, J = 3.4)<br>3.75(s, 2H, ); 3.73(s, 2H,); 2.81(s, 2H, d); 1.28(5, 6H, —CH$_3$) |
| 5 | B.P. 167° C.<br>IR: 1700(C=O) |
| 6 | B.P. 173° C.<br>IR: 1703<br>NMR: 8.25–8.0(m, 3H, chinol.); 7.9–7.2(m, 8H, 2Ar); 3.85(s; 2H, CH$_2$); 3.78(s, 2H, CH$_2$); 2.77(s, 2H, CH$_2$), 1.30s, 6H, 2CH$_3$); 12.0(b, COOH) |
| 7 | B.P. 164° C.<br>IR: 1702 (C=O)<br>NMR: 8.8–8.55(m, 2H AA'-Pyridyl), 7.8–7.3(m, 7H, BB'-Ar) 3.74(s, 4H, CH$_2$COO + CH$_2$); 2.78(s, 2H, CH$_2$); 1.28(6H, s, 2CH$_3$) 11.5(b, 6.14, COOH) |
| 8 | B.P. 137.6° C.<br>IR: 2950, 1708, 1599, 1557, 1445, 1412, 1284, 1218, 801, 693, (C=O: 1720)<br>NMR: 7.26–7.15(m, 5H, arom.); 6.79 + 6.61(AB, 2H, J = 3.7, —CH=CH—); 3.76(s, 2H, —CH$_2$—N—); 3.65(s, 2H, —CH$_2$C=O); 2.81(s, 2H, —CH$_2$);<br>1.61(9.44, J = 7.3, ethyl); 0.39(t, 6H, J = 7.3, ethyl) |
| 9 | B.P. 140–142° C.<br>IR: 3260(—NH—), 1722(—C=O), 1437(—SO$_2$—) 1327, 1113 |

TABLE 5-continued

| Compound of Example # | |
|---|---|
| | NMR: 7.4–7.1(m, 5H, Ar); 6.82/6.55(AB-System, $J_{AB}$ = 3.8Hz 3.72(s, 2H, $CH_2$); 3.71(s, 2H, $CH_2$); 3.21(s; 3H, $SO_2CH_3$), 2.82(s, 2H, $CH_2$), 1.619(q, 4H, 2-$CH_2$, J = 7.4Hz; 0.899(t, 6H, J = 7.4Hz, 2$CH_3$—) |
| 10 | B.P. 158–160° C.<br>IR: 3225(—NH—), 1721(—C=O); 1432, 1184, 1084(—$SO_2$)<br>NMR: 8.02(b, 1H; NH—); 7.9–7.8(m; 2H; AA') 7.4–7.1(m =, 7H, Ar + BB'); 6.740–6.446(AB, 2H, JAB = 3.7Hz); 3.58(s, 4H, 2-$CH_2$); 2.79 (s, 2H, $CH_2$), 2.45(s; 3H, Ar—$CH_3$); 1.57(q, 4H; 2$CH_2$); 0.861(t, 6H, 2$CH_3$) |
| 11 | B.P. 163° C.<br>IR: 3220, 2950, 1721, 1432, 1395, 1341, 1176, 1113, 971, 878<br>NMR: 7.31–7.14(m, 5H, arom.); 6.83 + 6.56(AB, 2H, J = 3.7Hz- —CHCH—); 3.72(s, 2H,); 3.69(s, 2H); 3.44(s, 3H, —$SO_2CH_3$); 2.84(s, 2H, —$CH_2$—); 1.30(s, 6H, —$CH_3$) |
| 12 | B.P. 188° C.<br>IR: 3235(—NH—), 1725(—C=O), 1442, 1166, 1083($SO_2^-$)<br>NMR: 8.1(b, 1H, —NH), 7.9–7.8(m, 2H, AA', Ar), 7.4–7.1(m, 7H, Ar + BB') 6.74, 2.82(s, 2H, $CH_2$); 2.29–2.41(m, 2H, $CH_2$—COOH) (6.45(AB, JAB = 3.75Hz); 3.58(s; 2H, $CH_2$); 3.56(s, 2H, $CH_2$) 2.80(s, 2H, $CH_2$), 2.45(s, 3H, Ar—$CH_3$); 1.25(s, 6H; 2$CH_3$) |
| 13 | B.P. 199° C.<br>IR:1704 (C=O)<br>NMR: 7.23-7.11(m, 5H, Ar); 6.80/6.61(AB, 2H, J = 3.8Hz, thien.); 3.71(s, 2H, $CH_2$); 3.06(t, 2H, $CH_2$, J = 6.7Hz), 2.79(s, 2H, $CH_2$), 2.36(t, 2H, J = 6.8Hz, $CH_2$); 1.24(s, 6H, 2$CH_3$) |
| 14 | B.P. 123° C.<br>IR: 1700 (C=O)<br>NMR: 7.3–7.15(m, 5H; Ph); 6.70($H_A$, 1H, $J_{AB}$ = 3.5Hz), 6.50($H_B$, 1H, $J_{AB}$ = 3.5Hz) 3.65(t, 2H, $CH_2$), 2.88(t, 2H, $CH_2$), 2.49/2.45(2 quin. 4H, 2$CH_2$) 2.35(t, 2H, $CH_2$), 2.14(t, 2H; $CH_2$); 1.77(quin. 2H, $CH_2$ |
| 15 | IR: 1703 (C=O)<br>NMR: 7.20–7.08(m, 5H, arom.); 6.80, 6.62(AB, 3.8Hz, Thiophen); 2.31–2.64(m, 4H, C-2 and $CH_2$—COOH); 2.70–3.10(m, 4H, C-1 and Py-$CH_2$); 3.91(t, 2H, J = 7Hz, C-3) |
| 16 | NMR: 7.21–7.0(m, 5H, Ar); 6.78, 6.61(AB, J = 3.8Hz, Thiophen-H); 6.30(q, 1H, J = 0.8Hz); 3.81(s, 2H, $CH_2$): 2.41(d, 3H, J = 0.8Hz) |
| 17 | B.P. <190° C. (Zers.)<br>NMR: 7.8(s, 1H, NH); 7.20–7.04(m, 5H, Ar); 6.78, 6.68(AB, J = 3.8Hz, Thiophen-H); 6.31(q, 1H, 0.8Hz); 3.78 (s, 2H, $CH_2$); 3.08(s, 3H, $CH_3$); 2.39(d, 3H, 0.8Hz) |

We claim:

1. Heterocyclic compounds of formula I:

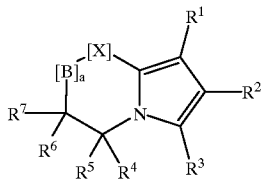

in which one of the radicals $R^1$, $R^2$ and $R^3$ stands for a mono- or bicyclic aromatic heterocyclic radical which includes at least one heteroatom selected from the group consisting of oxygen, nitrogen and sulfur and which is optionally condensed with a phenyl or napthyl radical and is optionally substituted by halogen, $CF_3$, alkyl or alkoxy, the second of the radicals $R^1$, $R^2$ and $R^3$ stands for an aryl radical, which optionally has one or two substituents which are selected from the group comprising halogen, CN, $CF_3$, $NO_2$, OH, alkoxy, $OCF_3$, alkyl and aryloxy, or for a mono- or bicyclic aromatic heterocyclic radical which includes at least one heteroatom selected from the group consisting of oxygen, nitrogen and sulfur and which is optionally condensed with a phenyl or napthyl radical and is optionally substituted by halogen, $CF_3$, alkyl or alkoxy, and the third of the radicals $R^1$, $R^2$ and $R^3$ stands for H, CHO, $CO_2H$, COO alkyl, COS alkyl, $COCO_2H$, $COCO_2$ alkyl or A-Y, A stands for $C_1$–$C_8$ alkylene or $C_2$–$C_8$ alkenylene, Y stands for $CO_2H$, $SO_3H$, $OPO(OH)_2$, $OP(OH)_2$, a group that represents an acid equivalent, COO alkyl, $SO_2O$ alkyl, CHO, OH, or $CONR^8R^9$, $R_8$ is hydrogen and $R_9$ is $SO_2C_1$–$C_8$ alkyl optionally substituted with halogen or $R_9$ is $SO_2$ phenyl optionally substituted with $C_1$–$C_8$ alkyl, $R^4$, $R^5$, $R^6$ and $R^7$, which may be identical or different, stand for H or alkyl, or two of these radicals stand for a chemical bond between the two ring atoms to which they are bonded and the other two have the meanings stated, or $R^4$ and $R^5$ together with the carbon atom to which they are bonded stand for a carbonyl group, X stands for $CH_2$, B stands for $CH_2$, and a stands for 0, or 1, and their optical isomers, salts and esters.

2. Compounds of claim 1 of formula I, in which one or two of the radicals $R^1$, $R^2$ and $R^3$ stand for a 5- or 6-membered aromatic heterocyclic radical, which as defined in claim 1 is optionally substituted and condensed.

3. Compounds of claim 2, wherein the heterocyclic radical is an optionally substituted thiophene, pyrrole, imidazole, thiazole, thiadiazole, furan, oxazole, isoxazole, pyridine, pyrimidine, benzofuran, or quinoline radical.

4. Compounds of claim 3, wherein the heterocyclic radical is a thiophene, halogen-substituted thiophene, furan, pyridine, benzofuran, or quinoline radical.

5. Compounds of claim 3, wherein one of the radicals $R^1$, $R^2$ and $R^3$ stands for the aforementioned heterocyclic radical and the second stands for phenyl, for phenyl substituted with one to three halogen atoms or $CF_3$, for thienyl, or for halogen-substituted thienyl.

6. Compounds of claim 2, wherein the third of the radicals $R^1$, $R^2$ and $R^3$ stands for A-Y.

7. Compounds of claim 6, wherein A stands for $C_1$–$C_8$ alkylene and Y stands for $CO_2H$, $COOC_1$–$C_8$ alkyl, $SO_3H$, $SO_3C_1$–$C_8$ alkyl, $CONR^8R^9$, $COCO_2H$ or $COCO_2C_1$–$C_8$ alkyl and $R_8$ is hydrogen and $R_9$ is $SO_2C_1$–$C_8$ alkyl optionally substituted with halogen or $R_9$ is $SO_2$ phenyl optionally substituted with $C_1$–$C_8$ alkyl.

8. A pharmaceutical composition comprising at least one compound of claim 1, in combination with pharmaceutically compatible vehicle and/or additive substances.

9. A method for preventing or treating allergically induced diseases or for treating diseases of the rheumatoid variety, comprising administering to a human or mammalian subject a pharmaceutically effective amount of the pharmaceutical agent of claim 8.

10. A process for preparing the compounds of claim 1, characterized in that a compound of the general formula II:

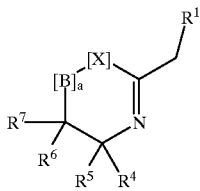

is reacted with a compound of the general formula III:

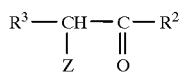

wherein in the above formulas two of the radicals $R^1$, $R^2$ and $R^3$ have the meanings recited in claim 1 and the third stands for a hydrogen atom, and Z stands for Cl or Br, to form a compound of the general formula Ia:

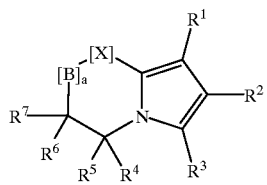

in which $R^1$–$R^7$, B, z and X have the meanings recited above, and into the compound obtained, a radical which corresponds to the meaning of the third of the radicals $R^1$, $R^2$ and $R^3$ is introduced if desired, optionally in a multistage reaction.

11. The process of claim 10, characterized in that for preparing the formula I compounds, in which the third of the radicals $R^1$, $R^2$ and $R^3$ stands for $CH_2COOH$, $CH_2COO$ alkyl or $COCO_2H$, a compound of formula Ia defined in claim 10 is reacted with oxalylchloride to form a formula I compound, in which one of the radicals $R^1$, $R^2$ and $R^3$ stands for $COCO_2H$, and optionally this compound is treated with a reagent which is suitable for reducing the keto group of the ketocarboxylic acid to a $CH_2$ group, so that a formula I compound is obtained in which one of the radicals $R^1$, $R^2$ and $R^3$ stands for $CH_2CO_2H$.

12. A compound as claimed in claim 1 wherein $R^1$ is phenyl, $R^2$ is 2-benzofuranyl, $R^3$ is $CH_2$—$CO_2H$, $R^4$ is hydrogen, $R^5$ is hydrogen, $R^6$ is $CH_3$, $R^7$ is $CH_3$, X is $CH_2$ and a is 0.

* * * * *